United States Patent [19]

Yafuso et al.

[11] Patent Number: 4,999,306
[45] Date of Patent: Mar. 12, 1991

[54] COMPOSITION, APPARATUS AND METHOD FOR SENSING IONIC COMPONENTS

[75] Inventors: Masao Yafuso, El Toro; Henry K. Hui, Laguna Niguel, both of Calif.

[73] Assignee: Minnesota Mining and Manufacturing Company, St. Paul, Minn.

[21] Appl. No.: 188,414

[22] Filed: Apr. 28, 1988

Related U.S. Application Data

[63] Continuation-in-part of Ser. No. 917,913, Oct. 10, 1986, Pat. No. 4,798,738.

[30] Foreign Application Priority Data

Oct. 7, 1987 [EP]  European Pat. Off. ........ 87308884.3

[51] Int. Cl.$^5$ ............................................ G01N 21/64
[52] U.S. Cl. ..................................... 436/68; 128/634;
250/227.14; 350/96.3; 356/39; 422/58;
422/82.06; 422/82.07; 436/163; 436/172
[58] Field of Search ............ 422/58, 68, 82.06, 82.07;
436/68, 163, 172; 128/634; 250/227, 461.1,
227.14; 350/96.3; 356/39

[56] References Cited

U.S. PATENT DOCUMENTS

| | | | |
|---|---|---|---|
| Re. 31,879 | 5/1985 | Lübbers et al. | 422/68 X |
| 3,449,080 | 6/1969 | Edwards | 436/74 |
| 3,904,373 | 9/1975 | Harper | 422/57 |
| 4,473,650 | 9/1984 | Wang | 432/2 |
| 4,543,335 | 9/1985 | Sommer et al. | 436/69 |
| 4,548,907 | 10/1985 | Seitz et al. | 436/163 |
| 4,557,900 | 12/1985 | Heitzmann | 422/55 |
| 4,577,109 | 3/1986 | Hirschfeld | 250/461.1 |
| 4,762,799 | 8/1988 | Seitz et al. | 422/68 X |
| 4,803,049 | 2/1989 | Hirschfeld et al. | 422/68 X |

*Primary Examiner*—David L. Lacey
*Assistant Examiner*—Jill Johnston
*Attorney, Agent, or Firm*—Gary L. Griswold; Walter N. Kirn; Dale E. Hulse

[57] ABSTRACT

A composition of matter useful for sensing the concentration of an ionic component in a medium comprising a cationic or anionic matrix material and a sensing component chemically bonded to the matrix material and being effective to provide a signal in response to the presence of the ionic component in the medium.

49 Claims, 1 Drawing Sheet

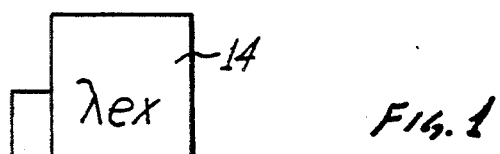
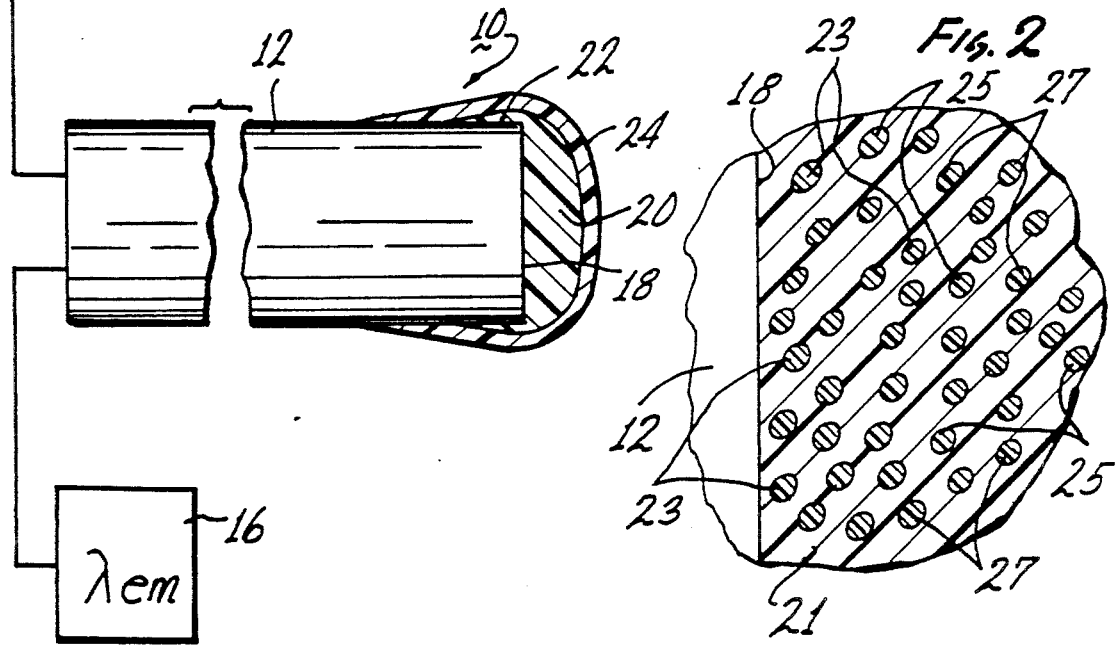
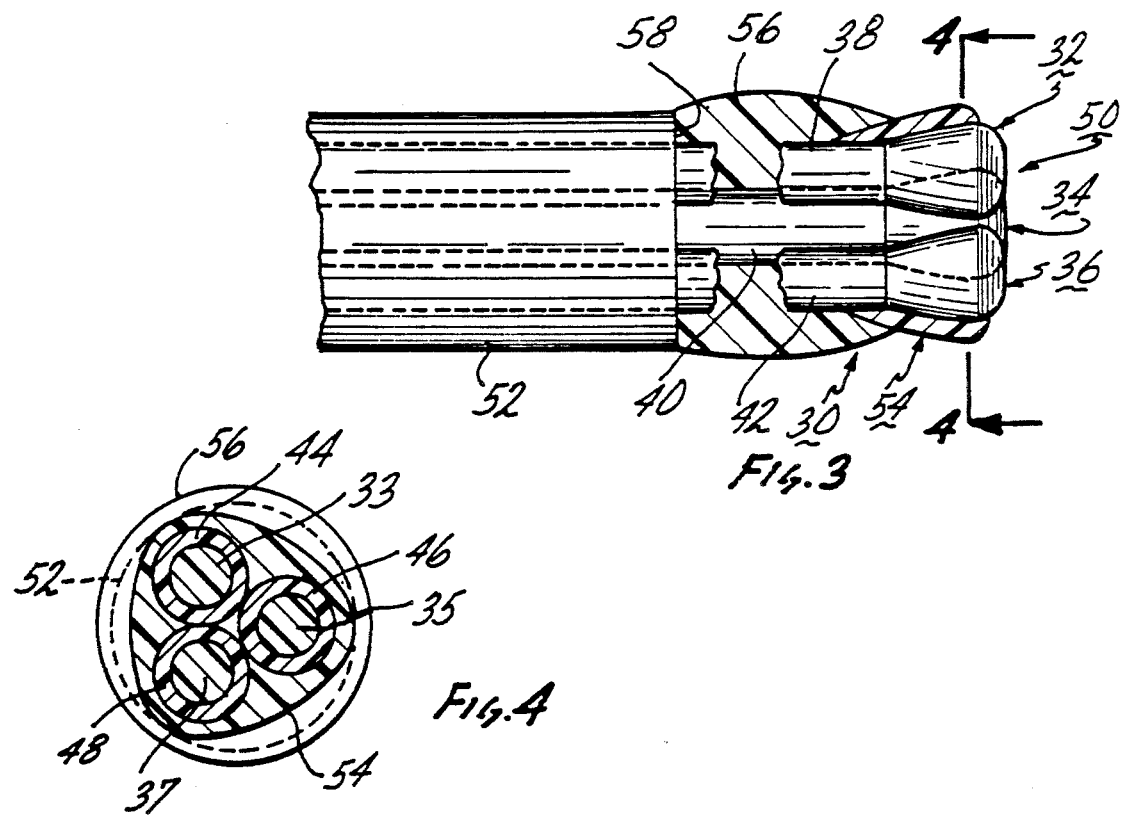

4,999,306

COMPOSITION, APPARATUS AND METHOD FOR SENSING IONIC COMPONENTS

RELATED APPLICATION

This application is a continuation-in-part of application Ser. No. 917,913, filed Oct. 10, 1986, now U.S. Pat. No. 4,798,738, which application is incorporated herein in its entirety by reference.

BACKGROUND OF THE INVENTION

This invention relates to a system for sensing ionic components. More particularly, the invention relates to compositions, apparatus and methods useful for sensing ionic components, e.g., hydrogen or hydroxyl ions-measured by pH, in fluids, such as blood.

It is often advantageous to determine the concentration of an ionic component in a given fluid. For example, medical diagnostic and/or treatment procedures may involve the determination of the pH value of a patient's blood or other bodily fluid. Such determinations may be made very frequently, even continuously, during treatment.

One problem which has arisen is that any one ionic component indicator, e.g., pH indicator, is effective over only its "effective indicator range", i.e., a limited range of concentrations of the ionic component, e.g., a limited pH range, where reliable determinations can be obtained using the given indicator. For example, each pH indicator has a unique pKa associated with a unique pH response range. Therefore, each pH indicator is useful over a limited pH range, e.g., of about one pH unit. Thus, if the concentration of the ionic component in a given medium is outside the "effective indicator range", reliable concentration determinations cannot be obtained without changing the indicator. A pH indicator, e.g., dye, with an appropriate pKa is needed for each pH range of interest. A different indicator, e.g., dye, with a different pKa is needed outside this range. It would be advantageous to use an indicator outside its "effective indicator range". For example, in the medical area, it may be useful to employ an indicator in the physiological range even though its normal "effective indicator range" is located outside this range.

Indicators are often used in combination with matrix materials, such as polymeric materials. For example, Seitz et al U.S. Pat. No. 4,548,907 teaches the use of a pH sensitive fluorophor (8-hydroxy-1,3,6-pyrenetrisulfonic acid) which is electrostatically bound to an ion exchange membrane, such as an anion exchanger. Seitz et al uses the ion exchange membrane to immobilize the fluorophor to measure physiological pH's by a ratioing technique.

Edwards U.S. Pat. No. 3,449,080 teaches a device for measuring the level of electrolyte in body fluid for diagnostic purposes which comprises a carrier containing a polymeric material having ion exchange characteristics which is capable of exchanging ions with the electrolyte whose level is to be measured, and a material which is color responsive to the extent of the ion exchange. In effect, the species the color of which the material is color responsive to is the product of the ion exchange. Wang U.S. Pat. No. 4,473,650 also discloses a system in which an ion exchange product is used to measure a characteristic of a test sample.

Sommer et al U.S. Pat. No. 4,543,335 discloses a method for preparing a device for the quantitative determination of heparin in mammalian blood plasma which involves coating a carrier matrix with a fluorogenic or chromogenic substrate solution. Buffer is included in two layers of the device because the rate of thrombin enzymatic reaction is pH dependent. The pH of the buffer in both layers is designed to maximize the reaction of thrombin and the substrate.

Harper U.S. Pat. No. 3,904,373 teaches bound pH indicators which include any complex comprising an organic species covalently coupled via a silane coupling agent to a carrier, preferably an inorganic carrier having available hydroxyl or oxide groups. Such inorganic carriers include glass silica gel, colloidal silica, woilastonite, and bentonite. Harper does not teach carriers which are anionic or cationic after the coupling. Further, Harper lists a large number of pH indicators, thus impliedly suggesting that each indicator is to be used for a different pH range. Harper does not teach extending the effective range of any pH indicator.

For biological fluids, a prior known sensor uses the fluorescent properties of a dye in conjunction with the ionic permeability of a preformed integral cellulose membrane sheet. In this sensor, the cellulose membrane is chemically treated so as to introduce covalent bondable groups onto the membrane. The dye is then covalently bonded to these groups to adhere the dye to the membrane. Substantially all the covalently bondable groups introduced onto the membrane are used to covalently bond the dye to the membrane. Thus, the dye is adhered to a substantially nonionic matrix material. A small disk is cut from the membrane sheet and is attached to a cassette in association with an optical fiber bundle also attached to the cassette. When the dye is excited by excitation light imposed on the dye along the fibers, it undergoes fluorescence, emitting a wavelength of light at a different wavelength than the excitation wavelength. The emission light is measured as an indication of the pH.

SUMMARY OF THE INVENTION

A new system for sensing or measuring the concentration of an ionic component in a medium has been discovered. This system, e.g. composition of matter, apparatus and method, utilizes at least one ionically charged matrix material to control the ionic environment to which an ionic component indicator or sensing component is exposed. Ultimately, the sensing component combined with an ionically charged matrix material is able to effectively sense or measure concentrations of ionic components over a broader concentration range and/or over a different concentration range relative to the same sensing component combined with a nonionic or ionically neutral matrix material. By controlling the charge density of the matrix material, the concentration range over which a given sensor is effective can be changed, as desired. Thus, a given indicator can be used to provide reliable concentration determinations even at concentrations which are outside the "effective concentration range" of the indicator.

In one broad aspect, the invention involves a composition of matter useful for sensing or measuring the concentration of an ionic component in a medium. This composition comprises a cationic or anionic matrix material and a sensing component chemically bonded, preferably covalently bonded, to the matrix material and being effective to provide a signal in response to the presence of the ionic component in the medium. An apparatus for measuring the concentration of an ionic component in a medium comprises a sensor means including the above-noted composition and signal means capable of transmitting the signal from the sensing component.

In another broad aspect, the invention involves a mixed composition useful for sensing or measuring the concentration of an ionic component in a medium. This composition comprises a combination of at least two of: (1) a cationic matrix material and a first sensing component associated therewith and being effective to provide a signal in response to the presence of the ionic component in the medium in a first concentration range; (2) a substantially nonionic matrix material and a second sensing component associated therewith and being effective to provide a signal in response to the presence of the ionic component in a second concentration range; and (3) an anionic matrix material and a third sensing component associated therewith and being effective to provide a signal in response to the presence of the ionic component in the medium in a third concentration zone. Preferably, the first, second and third sensing components are substantially identical. An apparatus for measuring the concentration of an ionic component in a medium comprises a sensor means including this mixture and a signal means capable of transmitting signals from the sensing components.

The present invention is particularly useful in sensing the concentration of hydrogen ions ($H+$) or hydroxyl ions ($OH-$). In this embodiment, the pH of the medium is the most often determined.

The signal provided by the sensing component or components in response to the presence of the ionic component in the medium preferably varies as the concentration of the ionic component in the medium varies. The sensing component is preferably an optical indicator, more preferably an absorbance indicator or a fluorescence indicator. Many sensing components useful to provide a signal in response to the presence of ionic components are conventional and well known in the art.

Any suitable sensing component may be employed in the present invention, provided that such sensing component can be effectively chemically bound to the desired matrix material. Suitable pH sensing components include many well known pH indicators and/or functionalized derivatives of such indicators. Among these pH indicators are hydroxypyrenetrisulfonic acid and salts thereof, phenolphthalein, fluorescein, phenol red, cresol red, pararosaniline, magenta red, xylenol blue, bromocresol purple, bromophenol blue, bromothymol blue, metacresol purple, thymol blue, bromophenol blue, tetrabromophenol blue, brom-chlorphenol blue, bromocresol green, chlorphenol red, o-cresolphthalein, thymolphthalein, metanil yellow, diphenylamine, N,N-dimethylaniline, indigo blue, alizarin, alizarin yellow GG, alizarin yellow R, congo red, methyl red, methyl orange, orange I, orange II, nile blue A, ethyl bis (2,4-dinitrophenyl) acetate, gamma-naphthoibenzein, methyl violet 6B, 2,5-dinitrophenol, and/or the various functionalized derivatives of the above species. Even when an indicator cannot be chemically bound unchanged with retention of indicator activity, one or more of its derivatives can often be chemically bound with satisfactory results.

Sensing components for other ionic components can be made from organic species which include fluorescein, diiodo-fluorescein, dichlorofluorescin, phenosafranin, rose bengal, eosin I bluish, eosin yellowish, magneson, tartrazine, eriochrome black T and others.

The preferred pH indicator selected from the group consisting of hydroxypyrenetrisulfonic acid, derivatives thereof and mixtures thereof.

The cationic and/or anionic matrix material useful in the present invention is preferably substantially insoluble in the medium being sensed or analyzed. Also, the matrix material should be permeable to the ionic component being sensed. That is, the matrix material should be structured s that the ionic component being sensed can physically permeate the matrix material. It should be noted that the charges on the matrix material may act to repel the ionic component. However, even in such event, the matrix material should be physically structured to be permeable to the ionic component, i.e., so that, the ionic component can substantially freely permeate the matrix material.

The matrix material is preferably a polymeric material. In one embodiment, the matrix material comprises a base polymer and a plurality of anionic or cationic groups, as desired. For example, the base polymer may be derivatized to chemically bond cationic or anionic groups to the base polymer. Macromolecular hydrophilic polymers which are substantially insoluble and permeable to the ionic component of interest are useful as base polymers in systems to be used in aqueous media. Such base polymers include, for example, cellulose, high molecular weight polyvinylalcohol (i.e., PVA), polyurethanes, quaternarized polystyrenes, sulfonated polystyrenes, polyacrylamides, polyhydroxyalkyl acrylates, polyvinyl pyrrolidones, hydrophilic polyamides, polyesters and mixtures thereof. In systems used to measure pH, cellulose, high molecular weight PVA and mixtures thereof are preferred.

The base polymer can be made anionic or cationic in character, as desired, using conventional and well known techniques. For example, the base polymer, or a functionalized derivative thereof may be reacted with an acidic component, such as an organic sulfonic acid, a carboxylic acid and the like, to form an anionic matrix material; or may be reacted with a basic component, such as an organic amine and the like, to form a cationic matrix material. Also noted above, such anionic and cationic matrix materials can be produced using conventional and well known procedures. Therefore, such procedures need not be discussed in detail here.

Chemical bonding of the sensing component to the matrix material can be accomplished either by direct coupling of the sensing component to reactive sites on the matrix material, as for instance, the hydroxyl groups on either cellulose or PVA, or through indirect coupling utilizing a substituent group which is coupled or chemically bound to the matrix material. For example, alkylamines can be first joined to at least a portion of the hydroxyl groups on the cellulose backbone by forming an ether between the alkyl portion of the alkylamine and the cellulose backbone. This leaves the amino functionality of the alkylamine available for reaction with the sensing component, e.g., dye, to join the sensing component to the matrix material or backbone. The use of alkylamines also acts to impart cationic character to the matrix material. The amount of alkyl amine employed can be controlled, as desired, to impact the desired degree of cationic character to the matrix material.

It is preferred to form a covalent bond between the optical indicator and the matrix material, either directly or indirectly through a substituent group. This assures that the sensing component is fixedly and irreversibly bound to the matrix material for improved performance of the sensor.

The substituent groups utilized in conjunction with the matrix materials are preferably organic and more preferably contain about 2 to about 20 carbon atoms. These substituent groups may be straight chain aliphatic, branched chain aliphatic, cyclo aliphatic or aromatic, or mixed aliphatic/aromatic. The substituent groups may include additional groups located thereon which are hydrophilic such as —OH, —$NO_2$, carboxyl, sulfonate or the like. In one embodiment, the substituent group is a aminoalkyl group. Preferably the aminoalkyl group includes about 2 to about 8, more preferably 2 or 3, carbon atoms.

In one embodiment, the starting material for the matrix material is a solid, finely divided polymeric material, e.g., a powder. However, the starting material for the matrix material may be present in a different state, such as a liquid. For convenience however, utilization of a solid powder polymeric material is preferred.

The sensing component is preferably an optical indicator, more preferably either an absorbance or a fluorescence indicator sensing component. Particularly good results are obtained with fluorescence indicators. For use with a pH sensor, sensing components such as hydroxypyrenetrisulfonic acid and its salts, fluorescein and beta-methylumbelliferone are preferred.

For an illustrative pH sensor of this invention, cellulose is utilized as the polymeric material. Aminoethylated cellulose is commercially available in a powdered form, as for instance from Sigma Chemical, St. Louis, Mo. If desired, free amine groups can be generated on aminoethylated cellulose. For example, if commercial aminoethylcellulose is utilized, the material as received from the manufacturer can be first treated to generate free amine groups. This is easily accomplished by simply treating the aminoethylcellulose with a sodium carbonate solution and drying.

The hydroxypyrenetrisulfonic acid, hereinafter referred to as HPTS, is first converted into an active species. It is of course realized that this material could be used as the free acid or as a suitable salt, e.g., an alkali metal salt or an alkaline earth metal salt. For use with aminoethylcellulose or other aminoalkylcellulose, a suitable active species is a sulfonic acid chloride. The HPTS is first acetylated to protect the hydroxy function of the HPTS and then it is converted to a suitable acid chloride.

The acid chloride derivative of the HPTS is reacted with aminoethylcellulose to covalently bond the HPTS to the cellulose backbone material utilizing sulfonylamido linkages. As is evident from the reaction of an acid chloride with an amine, hydrochloric acid is generated as a byproduct. This byproduct hydrochloric acid tends to react with other amine groups on the aminoethylcellulose. In view of this, the HPTS can be stepwise reacted with the aminoethylcellulose by first treating with a first batch of the HPTS acid chloride followed by treating this product with sodium carbonate solution, and further reacting with additional HPTS acid chloride. It is evident that the desired amount of HPTS which is to be loaded onto the cationic cellulose can be controlled by either stoichiometric control of the amount of HPTS which is added to any particular amount of cellulose or by control of the stepwise reaction noted above.

If desired, some of the amino groups can be blocked to control the cationic character of the matrix material. This blocking can be conveniently done by acetylating these amines, e.g., by utilizing an acetyl blocking group. Blocking substantially all of the remaining amino sites results in a substantially nonionic matrix material to which is covalently loaded a sensing component.

A stronger positively charged matrix material can be obtained by quaternarizing the unreacted amino groups on the matrix material. Conventional and well known quaternarizing reactions, e.g., utilizing alkyl halides such as methyl iodide, may be employed to produce quaternary amino groups on the matrix material. Such quaternarization preferably takes place after the cellulose matrix is regenerated. To increase the density of positively charged groups on the matrix more aminoalkyl groups can be introduced into the cellulose matrix by known methods.

If desired, an anionic matrix material may be utilized. Such an anionic matrix material may be produced by reacting the unreacted amino groups on the aminoalkyl cellulose (after chemically bonding the sensing component) with a di-functional acid derivative, such as a dicarboxylic acid anhydride or chloride. Again, to increase the density of anionic groups on the matrix additional aminoalkyl groups can be introduced into the matrix which can be reacted further with the difunctional acid derivatives.

The degree of cationic or anionic character of the matrix material can be controlled by controlling the density of aminoalkyl groups on the cellulose, and/or controlling the degree of quaternarization or acid reaction, respectfully, to which the aminoalkyl cellulose is subjected.

For strongly cationic matrices, such as found in commercially available ion exchange resins, it may not necessary to covalently bond HPTS. Due to the multianionic character of HPTS, ionic bonding may be sufficiently stable. The matrix can be formed on the optical surface and then dipped into a solution containing HPTS to form the sensing element.

Once the sensing component has been chemically bound to the matrix material, the material is preferably taken up into the solution. With cellulose, three basic types of solutions can be formed. The first of these is based on inorganic complexes, the second is based upon organic complexes and the third utilizes hemi esters or sulfur complexes.

The cellulose can be regenerated from any of these solutions by acid treatment. Such acid treatment typically entails utilizing a diluted acid such as the common mineral acids, e.g., sulfuric acid and the like.

In any event, after the cellulose is solubilized, an appropriate aliquot of the solubilized cellulose is then loaded onto an optical surface of an optical fiber or on an optical surface which interfaces with the optical fiber. The solubilized polymeric material is then regenerated so as to form a solid matrix of the sensing component-containing cellulose material on the optical surface of the optical fiber.

If desired, additional solubilized polymeric material can be added to the existing regenerated material already on the optical surface of an optical fiber. The further addition is followed by a further regeneration acid dip. This allows for the build up of a final matrix of a precise dimension. Since the solubilized cellulose adheres to both the regenerated cellulose matrix and to the glass of the optical fiber, it is possible to repeatedly add new aliquots of solubilized cellulose onto the existing regenerated cellulose to stepwise build up a sensor of any desired dimension.

For increased ion permeability of the final polymeric matrix on the end of the optical fiber, permeability enhancing agents can be added. These generally will be added either in the solvent for the cellulose, the regeneration solution for the cellulose or both of these. Suitable for use as such permeability enhancing agents are low molecular weight molecules which are hydrophilic and are water soluble. Such compounds include sugars, polyols and the like. For instance, glycerol can be added to both a solvent solution for the cellulose and to an acid regeneration bath. Another specific suitable permeability enhancing agent is low molecular weight water soluble PVA.

After regeneration of the cellulose on the optical fiber, the cellulose can be quaternarized or reacted with di-functional acid anhydrides or chlorides to obtain the desired cationic or anionic character. After this, the cellulose on the optical fiber can be overcoated with a suitable overcoating material serving to enhance certain properties of the sensor. An overcoat material would be chosen so as to be ionic component permeable as is the cellulose. Suitable for an overcoating material would be cellulose which is impregnated with carbon black and the like.

In use, the sensor on the end of an optical fiber is positioned in the appropriate test solution. If a fluorescent sensing component is utilized, an excitation light wavelength from a light source is channeled down the fiber toward the sensor. The light strikes the sensing component and the sensing component fluoresces and emits an emission light which is dependent on the concentration of the component of interest to which the sensing component is exposed. The emission light is then channeled back up the fiber to a light sensor for electrical readout of the same. This procedure is similar to that described in Lubbers et al, U.S. Pat. No. Re. 31,879 and Heitzmann, U.S. Pat. No. 4,557,900 each of which is incorporated in its entirety by reference.

BRIEF DESCRIPTION OF THE DRAWINGS

FIG. 1 is a schematic illustration of a sensor apparatus according to the present invention.

FIG. 2 is an enlarged, fragmentary sectional view of an alternate embodiment of the sensor apparatus shown in FIG. 1.

FIG. 3 is a side elevational view, partly broken away, showing a composite bundle of overcoated sensors.

FIG. 4 is an end elevational view in section about the line 4—4 of FIG. 3.

DETAILED DESCRIPTION OF THE DRAWINGS

FIG. 1 shows a suitable physical sensor 10 of the invention. An optical fiber 12 is connected to an appropriate light transmitting apparatus 14. The light transmitting apparatus 14 generates the excitation light. The optical fiber 12 is also connected to a light receiving apparatus 16. The light receiving apparatus 16 receives and analyzes the emission light from the fluorescent dye as is described in the above referenced Lubbers et al and Heitzmann patents.

Located on the optical surface 18 of the fiber 12 is a cationic polymeric matrix 20, as for instance, a cellulose matrix containing HPTS as a fluorescent pH indicator and quaternary amino groups to provide matrix 20 with the desired degree of cationic character. The matrix 20 adheres to the optical surface 18 and slightly down along the sides 22 of the end of the fiber 12. An opaque overcoating 24 can then be applied over the totality of the matrix 20 and down further along the side 22 of the fiber 12.

In use, the optical fiber 12 bearing the matrix 20 and the overcoat 24 thereon is placed in an appropriate solution. Excitation light of an appropriate wavelength from the light transmitting apparatus 14 is fed to the fiber 12. This interacts with the HPTS in the matrix 20 causing the HPTS to fluoresce. The emission light from the fluorescence is fed to light receiving apparatus 16.

The cationic character of matrix 20 tends to repel $H^+$ ions so that the pH in matrix 20 is increased relative to the pH in the solution. For example, when the pH in the solution is 6, the pH in the matrix is 7; and when the pH in the solution is 7, the pH in the matrix is 8. By using matrix 20 of controlled cationic character, one can effectively measure the pH of a solution having a pH in the range of 6 to 7 with a pH indicator having a range of 7 to 8 pH. In effect, the controlled ionic character of the matrix 20 allows one to controllably change the effective range of a pH indicator.

The present invention can be further illustrated by a matrix 20 which is anionic in character, having a controlled amount of free sulfonic acid or carboxylic acid groups. This anionic matrix 20 tends to attract $H^+$ ions so that the pH in matrix 20 is decreased relative to the pH in the solution. Thus, when the pH in the solution is 8 to 9, the pH in the anionic matrix 20 is 7 to 8, respectively. The anionic character of matrix 20 allows one to controllably change the effective range of the HPTS pH indicator from 7 to 8, to 8 to 9.

As appreciated by those of ordinary skill in the art, the cationic and anionic matrix materials set forth in the present specification and examples have cationic or anionic charge which is distributed within and throughout the matrix materials. As appreciated from the discussion above, the cationic or anionic charge of the matrix materials of the present invention is sufficient such that the apparent ionic concentration sensed by the sensing component within such matrix materials is either higher or lower (depending upon whether or not the matrix is cationic or anionic) than the actual ionic concentration in the tested medium.

The sensor 10 as is evident from FIG. 1 is of a size domain approximately that of the optical fiber 12. Thus, typically, the sensor 10 would only be slightly larger than a typical 125 micron diameter fiber. The thickness of the matrix 20 would be chosen so as to be approximately three to four mils thick.

FIG. 2 illustrates an embodiment of a sensor structured similarly to sensor 10 except that cationic polymeric matrix 20 is replaced by a hydrophilic matrix material 21 which includes cationic polymeric particles 23, nonionic polymeric particles 25 and anionic polymeric particles 27 randomly distributed throughout. Except as expressly stated herein, the sensor illustrated in FIG. 2 is structured and functions identically to the sensor 10 illustrated in FIG. 1.

Hydrophilic matrix material 21 can be any ionpermeable polymeric material which is compatible with the other components of the system. Examples of such materials include polyacrylamides, hydrogels, cellulose, polyurethanes, PVA and the like. The cationic polymeric particles 23 and anionic polymeric particles 27 can be produced in a manner similar to that discussed previously for preparing the cationic matrix material and anionic matrix material, respectively. Nonionic polymeric particles 25 are made from substantially nonionic polymers such as substantially nonionic cellulose. Each of the cationic polymeric particles 23, the nonionic polymeric particles 25 and the anionic polymeric particles 27 include covalently bonded HPTS as a fluorescent pH indicator. These particles have diameters in the range of about 1 micron or less to about 5 microns. Hydrophilic matrix material 21 itself is substantially free of HPTS.

The sensor including hydrophilic matrix material 21, cationic polymeric particles 23, nonionic polymeric particles 25 and anionic polymeric particles 27 is able to effectively monitor the pH of a medium over a range of 6 to 9 even though the normal effective range of HPTS is only 7 to 8.

FIGS. 3 and 4 show a sensor probe or bundle of individual sensors grouped together. Thus, in FIGS. 3 and 4 a sensor bundle 30 is shown. It includes three sensors, sensor 32, sensor 34 and sensor 36. Each of these includes an effective amount of HPTS as a fluorescent pH indicator. Sensor 32 includes an anionic cellulose matrix 33, sensor 34 includes a substantially nonionic cellulose matrix 35 and sensor 36 includes a cationic cellulose matrix 37. The HPTS indicator is covalently bonded to each of these matrices. If desired, the HPTS indicator may be ionically bonded to cationic matrix 37. Each of the sensors 32, 34, and 36 further includes suitable optical fibers, 38, 40 and 42, respectively. Located on each of these optical fibers and covering the specific components of the specific sensors 32, 34 and 36 are individual overcoatings 44, 46 and 48. Each of the overcoatings 44, 46 and 48 include an opaque agent in the overcoating material, such that individual sensors 32, 34 and 36 are optically isolated from one another.

Sensors 32, 34 and 36 are located together at the bundle tip 50 of sensor bundle 30. Optical fibers 38, 40 and 42 are arranged in a triangular arrangement as is evident from FIG. 4. Fibers 38, 40 and 42 are held together by a sleeve 52. Sleeve 52 is utilized to assist in introduction of the sensor bundle 30 into its working environment, e.g., intravenous positioning of sensor bundle 30.

Individual sensors 32, 34 and 36, having individual overcoating 44, 46 and 48, are positioned within sleeve 52 and a final bundle overcoating 54 is then applied along the sides of bundle tip 50. Bundle overcoating 54 fills in the voids between individual overcoatings 44, 46 and 48 forming a smooth surface at bundle tip 50 which inhibits thrombogenic reaction to sensor bundle 30. An epoxy coating 56 is positioned on sensor bundle 30 between the end 58 of sleeve 52 and bundle overcoating 54.

As is evident from FIG. 3, bundle overcoating 54 forms a smooth transition with epoxy coating 56 to sleeve 52. This substantially eliminates any pockets or voids that could provide a region of stasis where blood could coagulate. Finally, sensor bundle 30 may be covered with a blood compatible coating of a antithrombogenic agent (not shown in the drawings) that extends along the entire length of the bundle.

The three sensor bundle is able to effectively monitor the pH of a medium over a range of 6 to 9 even though the normal effective range of HPTS is only 7 to 8.

The following non-limiting examples illustrate certain aspects of the present invention.

EXAMPLE 1

5 grams of aminoethylcellulose is suspended in 100 mls of 2.5% sodium carbonate solution. It is stirred for 30 minutes, filtered and rinsed with 50 mls of deionized water. The filter cake is then suspended in 50 mls dry dimethylformamide. It is then filtered and again resuspended in dry dimethylformamide. This dehydrates the filter cake of the activated aminoethylcellulose. If the product is not being utilized immediately, it is stored dry.

EXAMPLE 2

10 grams of trisodium hydroxypyrenetrisulfonate, 50 mls of acetic anhydride and 1.6 grams of sodium acetate are added to 200 mls of dimethylformamide in a 500 ml flask. The flask is equipped with a condenser having a dry tube and a stirring bar. The contents of the flask are stirred at 50° C. to 70° C. for one to two hours. The reaction mixture is filtered and the filtrate collected. The filtrate is vacuum evaporated to yield a crude solid product. This crude solid product is dissolved into boiling methanol. The volume of the methanol is reduced to 100 mls and cooled. The first batch of product crystallizes out and is filtered. The methanol is reduced to approximately 20 mls to yield a second crop of product which is filtered and combined with the first batch and dried for twenty to forty minutes at 60° C.

EXAMPLE 3

2 grams of the trisodium acetoxypyrenetrisulfonate product from Example 2, and 6.6 grams of phosphorous pentachloride ($PCl_5$) are ground together with a mortar and pestle for 10 minutes. The homogenous solid mixture is then transferred to a 250 ml round bottom flask fitted with a condenser and drying tube. It is heated in boiling water for 60 minutes. The reaction mixture is then combined with 200 mls of hot toluene and vacuum filtered. The toluene from the filtrate is stripped off to recover the acetoxy-pyrenetrisulfonic acid chloride product.

EXAMPLE 4

100 mg of acetoxy-pyrenetrisulfonic acid chloride product from Example 3 is added to 100 mls of dry dimethylformamide. This is stirred for 45 minutes and 5 grams of activated aminoethylcellulose is added. This mixture is stirred for one hour, filtered and the filter cake washed with 50 mls of dimethylformamide. The filter cake is resuspended in 100 mls of 2.5% sodium carbonate solution and stirred for 30 minutes. It is filtered and the filter cake washed twice with 50 ml portions of deionized water. The water is then removed from the filter cake by three washings with dry dimethylformamide. The dried filter cake is then retreated a second time in 100 mls of dimethylformamide with 100 mg of acetoxypyrenetrisufonic acid chloride for 45 minutes. After the second treatment it is filtered and the cake washed with 2.5% sodium carbonate followed by two water washes. The product is stored over a dessicant under high vacuum to dry the same.

EXAMPLE 5

An inorganic zinc based solvent is prepared by dissolving 4.15 grams of zinc chloride in 100 mls of water. 50 mls of 2.2 M sodium hydroxide solution is added dropwise with stirring over ten minutes. The resulting product is centrifuged at 2000 RPM in a Beckman TO-6 centrifuge for ten minutes. The supernatant is decanted and 50 mls of 0.5 M sodium hydroxide is added to precipitate. This is agitated with a glass rod, recentrifuged and decanted again. This procedure is repeated twice more. 50 mls of cold 40% aqueous thylenediamine and 1 gram of glycerol are added to the final precipitate. This is mixed together by shaking. The product is then blanketed with nitrogen and stored in a refrigerator.

EXAMPLE 6

0.1 gram of HPTS bearing aminoethylcellulose from Example 4 above is dissolved by mixing with 1.9 grams of the final solution from Example 5, above, and stored protected in a freezer overnight. After standing overnight a viscous solution results. The solution is maintained in the freezer until used.

EXAMPLE 7

1 drop of the mixture of Example 6 is added to the end of a clean fiber tip of an optical fiber. This is dipped into a 5% sulfuric acid, 5% glycerol solution for 5 minutes to regenerate the cellulose. The fiber having the regenerated cellulose matrix located thereon is then rinsed with 1% sodium carbonate, 5% glycerol solution for 30 seconds. The thickness of the sensor is then measured wet. The desired thickness is 3 to 4 mils when wet. If the sensor is not of the desired thickness, a further drop of the product of Example 6 is added and the sensor is once again dipped into the sulfuric acid, glycerol bath. The sensor is once again washed with sodium carbonate and the thickness measured. A further amount of the sensor matrix can be regenerated on the sensor if, again, the desired thickness has not been reached.

Preferably, the sensing component e.g., HPTS, is utilized in a ratio in the range of about 1 mg to about 20 mg per 1 gram of polymeric material, e.g., aminoethylcellulose.

EXAMPLE 8

The regenerated cellulose sensor from Example 7 is contacted with sufficient acetic anhydride in the presence of pyridine at conditions effective to acetylate substantially all the amino groups present in the regenerated cellulose. The resulting sensor includes a substantially nonionic cellulosic matrix material. Alternately, the amino groups in the HPTS-containing aminoethyl cellulose may be effectively acetylated prior to the matrix material being solvated.

EXAMPLE 9

A sensor similar to that produced in Example 7 is contacted with a controlled amount of a dicarboxylic acid anhydride to convert the positively charged amine groups on the cellulosic matrix to negatively charged carboxylic acid amides. The resulting sensor has an anionic matrix material. The amount of dicarboxylic acid anhydride can be varied, as desired, to obtain the desired degree of anionic character in the cellulosic matrix.

EXAMPLE 10

A sensor similar to that produced in Example 7 is contacted with a controlled amount of methyl iodide at conditions effective to quaternarize a portion of the amine groups on the cellulosic matrix. The resulting sensor has a matrix material which is more strongly cationic, relative to the aminoethyl cellulose.

EXAMPLE 11

A small quantity of the mixture of Example 6 is placed on one side of an optically clear plate. This plate may be made of glass, polycarbonate and the like materials. This mixture is then contacted with a 5% sulfuric acid 5% glycerol solution for 5 minutes to regenerate the cellulose. The glass plate is then rinsed with 1% sodium carbonate, 5% glycerol solution for 30 seconds. This procedure is repeated until the thickness of the sensor is as desired.

The plate is then placed in abutting relation to the distal end of a clean fiber tip of an optical fiber so that the end of the fiber abuts the side of the plate opposite the side on which the sensor is located. With this configuration, the sensor is effective to measure the pH of liquid media coming in contact with the sensor.

EXAMPLE 12

The regenerated cellulose sensor/plate assembly from Example 11 is contacted with sufficient acetic anhydride in the presence of pyridine at conditions effective to acetylate substantially all the amino groups present in the regenerated cellulose. The resulting sensor includes a substantially nonionic cellulosic matrix material. Alternately, the amino groups in the HPTS-containing aminoethyl cellulose may be effectively acetylated prior to the matrix material being solvated.

EXAMPLE 13

A sensor/plate assembly similar to that produced in Example 11 is contacted with a controlled amount of a dicarboxylic acid anhydride to convert the positively charged amine groups on the cellulosic matrix to negatively charged carboxylic acid amides. The resulting sensor has an anionic matrix material. The amount of dicarboxylic acid anhydride can be varied, as desired, to obtain the desired degree of anionic character in the cellulosic matrix.

EXAMPLE 14

A sensor/plate assembly similar to that produced in Example 11 is contacted with a controlled amount of methyl iodide at conditions effective to quaternarize a portion of the amine groups on the cellulosic matrix. The resulting sensor has a matrix material which is more strongly cationic, relative to the aminoethyl cellulose.

While this invention has been described with respect to various specific examples and embodiments, it is to be understood that the invention is not limited thereto and that it can be variously practiced within the scope of the following claims.

What is claimed is:

1. A composition of matter useful for sensing the concentration of an ionic component in a medium, comprising:
   a matrix material having a cationic or anionic charge therewithin; and
   a sensing component chemically bonded to said matrix material and being effective to provide a signal in response to the presence of said ionic component in said medium;
   wherein said matrix material has sufficient cationic or anionic charge distributed within said matrix material such that the apparent ionic concentration sensed by said sensing component within said matrix material is higher or lower than the actual ionic concentration in said medium.

2. The composition of claim 1 wherein said sensing component is covalently bonded to said matrix material.

3. The composition of claim 1 wherein said ionic component is $H^+$ or $OH^-$.

4. The composition of claim 1 wherein said signal varies as the concentration of said ionic component in said medium varies.

5. The composition of claim 1 wherein said sensing component is an optical indicator.

6. The composition of claim 1 wherein said sensing component is a fluorescence indicator.

7. The composition of claim 1 wherein said matrix material is polymeric.

8. A composition of matter useful for sensing the concentration of an ionic component in a medium, said composition comprising a combination of at least two of:
(1) a matrix material having a cationic charge therewithin and a first sensing component within said cationic matrix material, said first sensing component within said cationic matrix material being effective to provide a signal in response to the presence of said ionic component in said medium in a first concentration range;
(2) a substantially nonionic matrix material and a second sensing component within said nonionic matrix material, said second sensing component within said nonionic matrix material being effective to provide a signal in response to the presence of said ionic component in said medium in a second concentration range; and
(3) a matrix material having an anionic charge therewithin and a third sensing component within said anionic matrix material, said third sensing component within said anionic matrix material being effective to provide a signal in response to the presence of said ionic component in said medium in a third concentration range;
wherein said first, second, and third sensing components are made from the same indicator material.

9. The composition of claim 8 wherein said first, second, and third sensing components are chemically bonded to said cationic, substantially nonionic, and anionic matrix materials, respectively.

10. The composition of claim 8 wherein said first, second, and third sensing components are covalently bonded to said cationic, substantially nonionic, and anionic matrix materials, respectively.

11. The composition of claim 8 comprising the combination of all of (1), (2), and (3).

12. The composition of claim 8 wherein said first, second, and third sensing components are optical indicators made from the same optical indicator material.

13. The composition of claim 8 wherein said first, second, and third sensing components are fluorescence indicators made from the same fluorescence indicator material.

14. The composition of claim 8 wherein said ionic component is $H^+$ or $OH^-$.

15. An apparatus for measuring the concentration of an ionic component in a medium, comprising:
sensor means including a matrix material having a cationic or anionic charge therewithin, and a sensing component chemically bonded to said matrix material and being effective to provide a signal in response to the presence of said ionic component in said medium, wherein said matrix material has sufficient cationic or anionic charge distributed within said matrix material such that the apparent ionic concentration sensed by said sensing component within said matrix material is higher or lower than the actual ionic concentration in said medium; and
signal means capable of transmitting said signal from said sensing component.

16. The apparatus of claim 15 wherein said sensing component is covalently bonded to said matrix material.

17. The apparatus of claim 15 wherein said ionic component is $H^+$ or $OH^-$.

18. The apparatus of claim 15 wherein said signal varies as the concentration of said ionic component in said medium varies.

19. The apparatus of claim 15 wherein said sensing component is an optical indicator.

20. The apparatus of claim 19 wherein said signal means comprises an optical fiber.

21. The apparatus of claim 15 wherein said sensing component is a fluorescence indicator.

22. The apparatus of claim 21 wherein said signal means comprises an optical fiber.

23. An apparatus for measuring the concentration of an ionic component in a medium, comprising:
sensor means including a combination of at least two of:
(1) a matrix material having a cationic charge therewithin and a first sensing component within said cationic matrix material, said first sensing component within said cationic matrix material being effective to provide a signal in response to the presence of said ionic component in said medium in a first concentration range; (2) a substantially nonionic matrix material and a second sensing component within said nonionic matrix material, said second sensing component within said nonionic matrix material being effective to provide a signal in response to the presence of said ionic component in said medium in a second concentration range; and (3) a matrix material having an anionic charge therewithin and a third sensing component within said anionic matrix material, said third sensing component within said anionic matrix material being effective to provide a signal in response to the presence of said ionic component in said medium in a third concentration range; wherein said first, second, and third sensing components are made from the same indicator material; and
signal means capable of transmitting said signals from said first, second, and third sensing components.

24. The apparatus of claim 23 wherein said first, second, and third sensing components are chemically bonded to said cationic, substantially nonionic, and anionic matrix materials, respectively.

25. The apparatus of claim 23 wherein said first, second, and third sensing components are covalently bonded to said cationic, substantially nonionic, and anionic matrix materials, respectively.

26. The apparatus of claim 23 wherein said sensor means includes the combination of all of (1), (2), and (3).

27. The apparatus of claim 23 wherein said ionic component is $H^+$ or $OH^-$.

28. The apparatus of claim 23 wherein said first, second, and third sensing components are optical indicators made from the same optical indicator material.

29. The apparatus of claim 28 wherein said signal means comprises an optical fiber.

30. The apparatus of claim 23 wherein said first, second, and third sensing components are fluorescence indicators made from the same fluorescence indicator material.

31. The apparatus of claim 30 wherein said signal means comprises an optical fiber.

32. A method for sensing the concentration of an ionic component in a medium, comprising:
contacting said medium with a composition comprising:
  a matrix material having a cationic or anionic charge therewithin; and
  a sensing component chemically bonded to said matrix material and being effective to provide a signal in response to the presence of said ionic component in said medium;
  wherein said matrix material has sufficient cationic or anionic charge distributed within said matrix material such that the apparent ionic concentration sensed by said sensing component within said matrix material is higher or lower than the actual ionic concentration in said medium; and
analyzing said signal to determine the concentration of said ionic component in said medium.

33. The method of claim 32 wherein said sensing component is covalently bonded to said matrix material.

34. The method of claim 32 wherein said ionic component is $H^+$ or $OH^-$.

35. The method of claim 32 wherein said signal varies as the concentration of said ionic component in said medium varies.

36. The method of claim 32 wherein said sensing component is a fluorescence indicator.

37. The method of claim 32 wherein said matrix material is polymeric.

38. The method of claim 32 wherein said sensing component is an optical indicator.

39. The method of claim 38 wherein said signal is transmitted prior to being analyzed.

40. The method of claim 39 wherein said signal is transmitted by an optical fiber.

41. A method for sensing the concentration of an ionic component in a medium, comprising:
contacting said medium with a composition comprising a combination of at least two of:
  (1) a matrix material having a cationic charge therewithin and a first sensing component within said cationic matrix material, said first sensing component within said cationic matrix material being effective to provide a signal in response to the presence of said ionic component in said medium in a first concentration range; (2) a substantially non-ionic matrix material and a second sensing component within said nonionic matrix material, said second sensing component within said nonionic matrix material being effective to provide a signal in response to the presence of said ionic component in said medium in a second concentration range; and (3) a matrix material having an anionic charge therewithin and a third sensing component within said anionic matrix material, said third sensing component within said anionic matrix material being effective to provide a signal in response to the presence of said ionic component in said medium in a third concentration range; wherein said first, second, and third sensing components are made from the same indicator material; and
analyzing said signal or signals provided by said sensing components to determine the concentration of said ionic component in said medium.

42. The method of claim 41 wherein said composition comprises the combination of all of (1), (2), and (3).

43. The method of claim 41 wherein said first, second, and third sensing components are chemically bonded to said cationic, substantially nonionic, and anionic matrix materials, respectively.

44. The method of claim 41 wherein said first, second, and third sensing components are covalently bonded to said cationic, substantially nonionic, and anionic matrix materials, respectively.

45. The method of claim 41 wherein said first, second, and third sensing components are fluorescence indicators made from the same fluorescence indicator material.

46. The method of claim 41 wherein said ionic component is $H^+$ or $OH^-$.

47. The method of claim 41 wherein said first, second, and third sensing components are optical indicators made from the same optical indicator material.

48. The method of claim 47 wherein each said signal is transmitted prior to being analyzed.

49. The method of claim 48 wherein each said signal is transmitted by an optical fiber.

* * * * *